(12) United States Patent
Higo et al.

(10) Patent No.: US 6,576,815 B1
(45) Date of Patent: Jun. 10, 2003

(54) PROMOTER SEQUENCE EXPRESSED IN ANTHERS AND POLLENS

(75) Inventors: Kenichi Higo, Tsukuba (JP); Masao Iwamoto, Tsukuba (JP)

(73) Assignee: National Institute of Agrobiological Sciences, Ibaraki (JP)

(*) Notice: Subject to any disclaimer, the term of this patent is extended or adjusted under 35 U.S.C. 154(b) by 0 days.

(21) Appl. No.: 09/700,971

(22) PCT Filed: Mar. 26, 1999

(86) PCT No.: PCT/JP99/01551
§ 371 (c)(1),
(2), (4) Date: Feb. 5, 2001

(87) PCT Pub. No.: WO00/58454
PCT Pub. Date: May 10, 2000

(51) Int. Cl.⁷ ............ A01H 1/00; A01H 5/00; C07H 21/04; C12N 15/82; C12N 5/04

(52) U.S. Cl. ........ 800/287; 800/278; 800/298; 536/24.1; 435/468; 435/419

(58) Field of Search ............... 800/287, 278, 800/298; 536/24.1, 23.1; 435/419, 69.1, 468

(56) References Cited

U.S. PATENT DOCUMENTS

| 568,904 A | 10/1896 | Heimberger |
| 5,639,948 A | 6/1997 | Michiels et al. |
| 5,689,049 A * | 11/1997 | Cigan et al. ............ 800/205 |

FOREIGN PATENT DOCUMENTS

| EP | WO/92/13956 | 2/1992 |
| EP | WO/96/17945 | 12/1995 |
| JP | 6-504910 | 6/1994 |
| JP | 10-51983 | 10/1998 |

OTHER PUBLICATIONS

Oommen et al., The Elicitor–Inducible Alfalfa Isoflavone Reduction Promoter Confers Differnet Patterens of Deveopmental Expression in Homologous and Heterologous Transgenic Plants, Dec. 1994, The Plant Cell, vol. 6, pp. 1789–1803.*

Higo et al., Cloning and characterization of the rice CatA catalase gene, a homologue of the maize Cat3 gene, 1996, Plant Molecular Biology, vol. 30, pp. 505–521.*

Hiromi, Higo et al., "Cloning and Characterization of the rice GatA catalase gene a homologue of the maize Cat3 gene" *Plant Molecular Biology,* vol. 30 (1996), p. 505–521, Refer to Abstract, Materials and methods, Results, Discussion.

Albani, Diego et al., "Characterization of a pollen–specific gene family from *Brassica napus* which is activated during early microspore development" *Plant Molecular Biology,* 15: 605–622, 1990.

* cited by examiner

*Primary Examiner*—Elizabeth F. McElwain
*Assistant Examiner*—Stuart Baum
(74) *Attorney, Agent, or Firm*—Fay, Sharpe, Fagan, Minnich & McKee LLP (57) ABSTRACT

The present invention provides methods and composition for specific expression of a heterologous gene in the anthers and/or pollen of a plant. Specifically, this invention provides a recombinants expression vector comprising the rice CatA gene promoter, or functionally equivalent variant thereof, operably linked to a heterologous gene. The invention also provides male sterile plants produced using the expression vector.

2 Claims, 4 Drawing Sheets

SEQUENCE LISTING

```
<160> NUMBER OF SEQ ID NOS: 2

<210> SEQ ID NO 1
<211> LENGTH: 1901
<212> TYPE: DNA
<213> ORGANISM: Oryza sativa
<220> FEATURE:
<221> NAME/KEY: promoter
<222> LOCATION: (1)..(1901)

<400> SEQUENCE: 1
```

-continued

```
tgtgcccacc acagcacacc tatcgttatc atcagcgtgg actaagaaca gaacaatttc      60
tcatcttttg tttcctgaga agtttagacc accaagatat atgctgatga tgctgtagat     120
agctagctag ttttgcaatt acttatgggt tgcatcacaa tcagggtctg tttagttccc     180
aaacaaaatt tttcacgctg ttacatagga tgtttggaca catgcataga gtactaaatg     240
tagaaaaaaa acaattaaac atttcgcctt gaaattacga gacaaatctt ttaagcctaa     300
ttgcgccatg atttgacaat ttggtgctac aataaatatt tgctaataat agattaatta     360
ggcttaataa attcgtcttg cagtttccag acggaatctg taatttattt tatgagatac     420
agctgcttcg atcttccatc acatattcag accgtaccta atctgaaagg ttagtaattt     480
gaactgcgta gtaatgctac aagtaaatc aatcatcatc atcttgaatt ggttcctctt      540
atagcactag gtaaaagac aagggtgcat tctggctggg ctgtgttcga taaggagtt       600 tgactgagct agttagtggc atgaaaaccg aacaggtga atagtacatg ataaactcag      660
tattacctat tataaacttg aaaactaaat ttatttaaaa ttttaaagac tagcaaagta    720
acgtgctctg caacggacgg atttttaaaag atttatgtga atttcttgat ttagaaattg  780
tatttgtcaa acataattgc aatcaaacat ccaatagaaa accaaaccac acacaaagat    840
gtatttatgt agcattagaa gatctcacca actctaaatg atggtagatt caccatcacc    900
attaaattct tttatatagt ataaaaagat tttgtacgaa acacactgtt tatagcttac    960
agtttgagaa acgtgtatgt ttatgataaa cgaagggtgt agctgagcca tagctagcta  1020
gcacaaagag cacctcgttc ttacagaata attaagcagc ctgaaattaa tctgagaaac  1080
aagaaagaaa atgcagagac gttagctgca actgcaatca tgtcaaactt tggccgaccg  1140
atcaagagaa aggggatgag ctaagctatc gatggcagca attcggcgcc gttgaaatca  1200
atcgaagaga tatgatccga tgatctgatc tgatctgacg atggacatgc agtgatggca  1260
cgcagctagt gagcactgat gaagtgatga cactccatgc atccaatcca ggcaatgcat  1320
gtatttcctt tccacacgag gggggcccac atccacctca ccttatcctc gtccagttcc  1380
tgtgggaccc aaccatgcag tatggccacc cgggcccacc agtcagtgtg tggcaccggt  1440
ctccggtaag ctcaccgggg aggtcagtgc tcctcaccac ctcccgctat ataaccttta  1500
ggcaggctgt ctcaccgagc aagctggaga gctagcagaa acaaacccct ctcactccca  1560
gatacctgct gctgccacta gcccactacc atggatcctt gcaaggtcag tcactcagtg  1620
actagtgaga ctaaatctac ttaatcttgt agttaataat tgaggtttca tttagctagt  1680
tgtgtagatt caagagagag cttaacttct tatagaatat ttggtcgatt atcagaaact  1740
tcctgaaata acctagatta tcgactagat tctacgaata tttctttttt agtctcaagc  1800
tcttcaaaca tgcatggctg gttgattcag ctagtcgatc attaagtata taattaatta  1860
attaattaat agtaatacgt gctacccatg cagttccggc c                      1901
```

<210> SEQ ID NO 2
<211> LENGTH: 4670
<212> TYPE: DNA
<213> ORGANISM: Oryza sativa

<400> SEQUENCE: 2

```
tgtgcccacc acagcacacc tatcgttatc atcagcgtgg actaagaaca gaacaatttc      60
tcatcttttg tttcctgaga agtttagacc accaagatat atgctgatga tgctgtagat     120
agctagctag ttttgcaatt acttatgggt tgcatcacaa tcagggtctg tttagttccc     180
```

-continued

| | |
|---|---|
| aaacaaaatt tttcacgctg ttacatagga tgtttggaca catgcataga gtactaaatg | 240 |
| tagaaaaaaa acaattaaac atttcgcctt gaaattacga gacaaatctt ttaagcctaa | 300 |
| ttgcgccatg atttgacaat ttggtgctac aataaatatt tgctaataat agattaatta | 360 |
| ggcttaataa attcgtcttg cagtttccag acggaatctg taatttattt tatgagatac | 420 |
| agctgcttcg atcttccatc acatattcag accgtaccta atctgaaagg ttagtaattt | 480 |
| gaactgcgta gtaatgctac aaggtaaatc aatcatcatc atcttgaatt ggttcctctt | 540 |
| atagcactag gtaaaaagac aagggtgcat tctggctggg ctgtgttcga taaaggagtt | 600 |
| tgactgagct agttagtggc atgaaaaccg aacaggtga atagtacatg ataaactcag | 660 |
| tattacctat tataaacttg aaaactaaat ttatttaaaa ttttaaagac tagcaaagta | 720 |
| acgtgctctg caacggacgg atttttaaaag atttatgtga atttcttgat ttagaaattg | 780 |
| tatttgtcaa acataattgc aatcaaacat ccaatagaaa accaaaccac acacaaagat | 840 |
| gtatttatgt agcattagaa gatctcacca actctaaatg atggtagatt caccatcacc | 900 |
| attaaattct tttatatagt ataaaaagat tttgtacgaa acacactgtt tatagcttac | 960 |
| agtttgagaa acgtgtatgt ttatgataaa cgaagggtgt agctgagcca tagctagcta | 1020 |
| gcacaaagag cacctcgttc ttacagaata attaagcagc ctgaaattaa tctgagaaac | 1080 |
| aagaaagaaa atgcagagac gttagctgca actgcaatca tgtcaaactt tggccgaccg | 1140 |
| atcaagagaa aggggatgag ctaagctatc gatggcagca attcggcgcc gttgaaatca | 1200 |
| atcgaagaga tatgatccga tgatctgatc tgatctgacg atggacatgc agtgatggca | 1260 |
| cgcagctagt gagcactgat gaagtgatga cactccatgc atccaatcca ggcaatgcat | 1320 |
| gtatttcctt tccacacgag gggggcccac atccacctca ccttatcctc gtccagttcc | 1380 |
| tgtgggaccc aaccatgcag tatggccacc cgggcccacc agtcagtgtg tggcaccggt | 1440 |
| ctccggtaag ctcaccgggg aggtcagtgc tcctcaccac ctcccgctat ataaccttta | 1500 |
| ggcaggctgt ctcaccgagc aagctggaga gctagcagaa acaaacccct ctcactccca | 1560 |
| gatacctgct gctgccacta gcccactacc atggatcctt gcaaggtcag tcactcagtg | 1620 |
| actagtgaga ctaaatctac ttaatcttgt agttaataat tgaggtttca tttagctagt | 1680 |
| tgtgtagatt caagagagag cttaacttct tatagaatat ttggtcgatt atcagaaact | 1740 |
| tcctgaaata acctagatta tcgactagat tctacgaata tttctttttt agtctcaagc | 1800 |
| tcttcaaaca tgcatggctg gttgattcag ctagtcgatc attaagtata taattaatta | 1860 |
| attaattaat agtaatacgt gctacccatg cagttccggc cgtcgagctc gttcgacacg | 1920 |
| aagacgacga cgacgaacgc gggagctccg gtgtggaacg acaacgaggc gctgacagtg | 1980 |
| gggcccaggg ggccgatcct cctcgaggac taccacctga tcgagaaggt ggcgcacttc | 2040 |
| gcccgggagc gcatcccgga gcgcgtggtc cacgcccgcg cgcctccgc caagggcttc | 2100 |
| ttcgagtgca cccacgacgt caccgacatc acctgcgccg acttcctccg gtccccgggc | 2160 |
| gcccagaccc ccgtcatcgt ccgcttctcc accgtcatcc acgagcgcgg cagcccggag | 2220 |
| acgatccgcg acccgcgcgg gttcgccgtc aagttctaca cccgcgaggg caactgggac | 2280 |
| ctcctcggca caacttccc cgtcttcttc atccgcgacg gcatcaagtt ccccgacgtc | 2340 |
| atccacgcct tcaagcccaa cccgcgctcc catgtccagg agtactggag ggtcttcgac | 2400 |
| ttcttgtccc accaccccga gagcctccac accttcttct tcctcttcga cgacgtcggc | 2460 |
| atccccaccg attaccgcca catggacggc ttcgcgtca cacctacac cttcgtcacc | 2520 |
| cgcgacgcca aggccaggta cgtcaagttc cactggaagc ccacctgcgg cgtcagctgc | 2580 |

-continued

```
ttgatggacg acgaggccac gctcgtcggc ggcaagaacc acagccacgc cacccaggac    2640
ctctacgact ccatcgccgc cggcaacttc cccgagtgga agctgttcgt ccaggtaggt    2700
gatcatccag aaattaacgc ctatacgatc tgagttcgaa gccgcagtac tccttctaat    2760
taattattta atactgttag gtgatcgacc cggaggagga ggagaggttc gacttcgacc    2820
cgctggatga caccaagaca tggccggagg acgaggtgcc gctccggccc gtggggcgcc    2880
tcgttctcaa ccgcaacgtc gacaacttct tcaacgagaa cgagcagctg gcgttcgggc    2940
cggggctggt ggtgccgggg atctactact ccgacgacaa gatgctgcag tgcagggtgt    3000
tcgcgtacgc cgacacgcag cgctacaggc tggggccaaa ctacctgatg ctgccggtga    3060
acgcgcccaa gtgcgcccac cacaacaacc actacgacgg cgccatgaac ttcatgcacc    3120
gggacgagga ggtggactac tacccatcgc gccacgcgcc gctccgccac gcgccgccga    3180
cgcccatcac gccgcgcccc gtggtgggga ggaggcagaa ggcgacgata cacaagcaga    3240
acgacttcaa gcagcccggg gagaggtaca ggtcgtgggc gccggataga caggagaggt    3300
tcatcccct tcgccggcga gtcgcgcacc ccaaggtctc ccctgagctc cgcgccatct    3360
gggtcaacta cctctcccag gtaattcata ccagcaattt agtattacct ccattttgt     3420
ttttatgaca ctactagtta aagtttgaac taatcaacgt catataaaaa aaacggaggg    3480
agtagttatt agtaatgatt aattgttttc tcttagttaa tccacatgat taacaccatg    3540
tttagcacaa cagttttatg aatccataga taaattattt aatcctattt tatatgaaat    3600
ataaatttt aaaccactgt agagaatttg aaattaatat gacttaatcg ctattaattt     3660
gcactaattc cggcaaaaaa agctattaat ttgcactaac tatgtaatta actcatttac    3720
ttcatgcagt gtgatgagtc gttggggggtg aagattgcga ataggctcaa cgtgaagcca   3780
agcatgtgaa gaaactaagg cacaagaatg catcatctct tgttaattaa ttggagtact    3840
accaaccaaa taaggccaga caatgtcaga tgcacgcatc ttctgttgtc gttgggccat    3900
cttttgtatg catcctattg ttaattacta gtacatgata tccaagtgat catcagcaag    3960
gctacagaaa ttctgtaata cgataaatta aaagaaacca aaatggagcc tgcatatgtg    4020
taacttaatt aatgtactgg cgtattaatg ccactgctgc atgttgtaat actccatcaa    4080
agagtctatt actattaagt atttaaatta tcacttcaat ggtctctttt ttttttccca    4140
aaccataggt ctatatacga accatatcta cgacatcagt ggtttaatta tcatgtttga    4200
caccgccaac ttcatacaga aactctacct caacattttg tttctccgct atacttacaa    4260
tgactttaat tagggaatgt gattgctgtg atattgagaa tggtaatatg ccgtctgact    4320
ttgagttctt tctaatttct taaaatcaat ttttaagctg agttatatca tgatcccagc    4380
cttacataac cttttggagc ggcaatgaaa caactgtgac ccacacagcg agtatattca    4440
ttggcgctga gttgttcgtg tcgatatgaa aacgaaataa aaacaaacct gtttatggta    4500
atgataatta atatctagtt ggatgaatca ttaatttttt ttatcttcat tccaaatttc    4560
agattaacca ataaaccatg ttaccggtgc tatcacctat catttactac gttgttcaaa    4620
caaaaatatg gtagattaat tctagcaccg tgaaagatgc aaatcgaatt               4670
```

PROMOTER SEQUENCE EXPRESSED IN ANTHERS AND POLLENS

This application is a 371 of PCT/JP99/01551 Mar. 26, 1999.

TECHNICAL FIELD

The present invention relates to the breeding of a useful plant utilizing a promoter of a plant gene. More specifically, the present invention relates to the breeding of a useful plant by utilizing a promoter gene of catalase gene A (hereinafter referred to as "CatA") from rice.

BACKGROUND ART

It is known that an F1 hybrid (first filial generation) which is created through intercultivar crossing may exhibit properties superior to those of its parents, and this has conventionally attracted much attention as a method of breeding crops. As for crops such as rice which experience self-pollination, methods for creating male sterile lines, whose pollen does not have fertility, have been studied as one of the techniques necessary for utilizing this property. Conventionally, plant genetic resource has been searched for male sterile lines, or male sterile lines have been selected by inducing mutagenesis. However, it is not easy to introduce such genes into practical cultivars, and the applications are limited.

Recently, as a method utilizing biotechnology, a method has been proposed in which a promoter that induces expression in anthers and/or pollen is ligated with a gene having a function of inhibiting the formation of such organs (e.g., a gene coding for nuclease, protease, glucanase, etc.) and is introduced into a plant, whereby the formation of fertile pollen is inhibited (for example, Mariani et al., Nature 347:737–741(1990)). Alternatively, methods which involve transcribing an anti-sense RNA of a gene to be expressed at the time of formation of such organs, or introducing a ribozyme which decomposes such mRNAs, by utilizing a promoter which induces expression in anthers and/or pollen, are regarded as promising.

Several kinds of promoters of genes which induce expression in anthers and/or pollen are known for tomato, *Arabidopsis thaliana*, maize, and the like (for example, Twell et al., Plant Physiol. 91:1270–1274(1989); Paul et al., Plant Molecular Biology 19:611–622(1992): Guerrero et al., Mol. Gen. Genet. 224:161–168(1990)). However, there is a problem in that their activity is too low to put them into practical use. Furthermore, in order to artificially control the formation of anthers and/or pollen, it would be very useful if a promoter which functions in any of the developmental stages of these organs was isolated and characterized, and a cassette containing a highly-active promoter could be created.

Accordingly, it would significantly contribute to the breeding of useful plants, including crops such as rice, if a promoter for anthers and/or pollen which is highly active and permits practical use could be obtained from rice genes.

DISCLOSURE OF THE INVENTION

The present invention relates to the breeding of a plant through genetic engineering techniques, and has an objective of providing an expression cassette for expression in plants and a recombinant plasmid which contain a plant gene promoter having a high activity in anthers and/or pollen, as well as a method for utilizing the same.

The inventors found that the catalase A (CatA) gene from rice exhibits a high promoter activity in anthers and pollen, and accomplished the present invention based on this information.

The present invention provides an expression cassette for expression in plants which allows a heterologous gene to be specifically expressed in anthers and/or pollen. This expression cassette contains a rice CatA gene promoter having a sequence shown as SEQ ID NO: 1, or a sequence which includes a portion thereof and which has a promoter activity equivalent to that of the sequence shown as SEQ ID NO: 1, and a site for inserting a heterologous gene such that the heterologous gene is expressibly linked to the promoter. Herein, the sequence shown as SEQ ID NO: 1 is a sequence including the 5' upstream region and the first intron of rice CatA structural gene.

The present invention also provides a recombinant plasmid for allowing a heterologous gene to be specifically expressed in anthers and/or pollen. The recombinant plasmid contains a rice CatA gene promoter having a sequence shown as SEQ ID NO: 1, or a sequence which includes a portion thereof and which has a promoter activity equivalent to that of the sequence shown as SEQ ID NO: 1, and a heterologous gene which is expressibly linked to the promoter.

Furthermore, the present invention provides a method for introducing into a plant a heterologous gene which is desired to be specifically expressed in anthers and/or pollen. This method includes the step of transforming a plant cell with the aforementioned recombinant plasmid, and the step of redifferentiating the transformed plant cell to obtain a plant body.

The aforementioned heterologous gene may be a gene which has a function of inhibiting the formation of anthers and/or pollen. By using such a gene in the aforementioned method, a male sterile plant can be created. In the aforementioned method, the plant cell may be either a monocotyledonous cell or a dicotyledonous cell.

BEST MODES FOR CARRYING OUT THE INVENTION

Hereinafter, the present invention will be described in more detail.

(Isolation of Rice CatA Gene Promoter)

Methods for isolating the catalase A (CatA) gene from rice and the base sequence of the genomic CatA gene including the promoter region according to the present invention have been published by the inventors in the proceedings of the 1992 meeting of JAPAN SOCIETY FOR BIOSCIENCE, BIOTECHNOLOGY, AND AGROCHEMISTRY: Journal of JAPAN SOCIETY FOR BIOSCIENCE, BIOTECHNOLOGY, AND AGROCHEMISTRY 66(3), 488 (1992), and Higo et al., Plant Molecular Biology 30:505–521(1996). However, the presence or absence of CatA gene expression in anthers and pollen, and the analysis of any transformed rice have not been published.

Rice CatA gene promoter can be screened from a genomic library of rice. A genomic DNA library of rice (Rice Genomic Library) which is commercially available from CLONTECH Laboratories Inc., Palo Alto, Calif. in the US can be used.

As a probe for the screening, rice CatA cDNA which has been isolated by the inventors can be used. Methods for isolating rice CatA cDNA and its base sequence have already been published by the inventors (Mori et al., Plant Molecular Biology 18:973–976(1992)).

First, a rice genomic gene library prepared by using phage λ is transfected into $E.$ $coli$ so as to allow plaques to form. Following a usual method, the plaques are transferred onto a membrane such as nitrocellulose, and then hybridized with a labeled probe for the screening. After the hybridization is completed, the membrane is washed and subjected to autoradiography. DNA is prepared from the phages which are confirmed to have hybridized.

The prepared phage DNA is digested by a combination of appropriate restriction enzymes, and the digest is separated by agarose gel electrophoresis. The separated DNA fragments are transferred onto a nylon membrane, and allowed to hybridize with the aforementioned probe for the screening, and are screened on the basis of signal intensities and differences in band patterns.

It is presumable that the clones which give the strongest signal contain the CatA gene, whereas clones which give a weaker signal contain genes which are similar to but are not CatA. Based on band pattern comparison, clones in which a portion of their genes has been deleted can be distinguished. Furthermore, by creating a physical map of the clones based on band patterns, clones in which the 5' upstream region of their structural gene is about 1.5 Kbp long—which are presumed to constitute a promoter—can be identified.

Thus, a complete CatA genomic gene can be isolated.

By comparing the base sequence of the CatA genomic gene against the base sequence of CatA cDNA, a promoter region can be identified. In the case where the genomic gene has introns, the promoter sequence may include not only the 5' upstream region of the structural gene but also regions such as the first intron.

(Identification of Promoter Activity Portions Based on GUS Activity Measurement)

Once the promoter region of the CatA gene is identified, its sequence may be cut out and ligated to an expression vector for expression in plants. In order to evaluate the activity of the ligated promoter, a plasmid may be prepared in which a reporter gene, such as a gene which codes for an appropriate enzyme, is ligated downstream of that promoter. This plasmid is introduced into a plant cell, and the gene expression is observed by measuring enzymatic activities, for example. In the case where a plant is used as a host, it is commonplace to take measurements by using a plasmid such as pBI221, for example, relying on the expression of β-glucuronidase (GUS) as an index. In the present specification, too, a method of taking measurements based on GUS expression is applicable.

GUS activity can be measured by basically following the method of Jefferson et al. (EMBO J 6:3901–3907(1987)). Specifically, a protoplast extract which is equivalent to a protein mass of 50 μg, 25 μl of 20 mM 4-methyl umbelliferryl glucuronide (4MUG), an extraction buffer, and 100 μl of methanol for suppressing any GUS-like activities inherent in plant tissue (Kosugi et al., Plant Science 70:133–140 (1990)) are added, and after the total amount is adjusted to 500 μl, an incubation is carried out at 37° C. Two hours later, 200 μl is collected from the reaction solution. To this, 0.8 mL of 0.2 M $Na_2CO_3$ is added to stop the reaction. With a fluorospectrophotometer, 455 nm fluorescence is measured by using 365 nm excitation light. The enzymatic activities are indicated in terms of 4-MU pmol/min/mg protein.

Plasmids in which the GUS gene is fused with various deletion mutants of the promoter region of the CatA gene, e.g., the CatA gene promoter region having been deleted to various lengths from the 5' upstream side, are used to measure their promoter activities, whereby the portions required for this activity and the like can be identified. Techniques for identifying such active portions are known to those skilled in the art. Therefore, for example, the present invention encompasses those sequences which are obtained by removing sequences not required for the CatA gene promoter region and which have an activity equivalent to that of the CatA gene promoter.

Once the CatA gene promoter region and its active portions are identified, their sequences may be further modified to enhance their promoter activity or change their specificity with respect to the expressed tissue. For example, the present invention encompasses a sequence which is obtained by partially modifying the CatA gene promoter region or active portions thereof and which still has an activity equivalent to that before the modification.

A promoter region having the sequence shown as SEQ ID NO: 1 specifically expresses its activity in anthers and/or pollen. Therefore, in the present specification, an "equivalent" promoter activity means a level of activity which is at least similar to the level of activity of a reference promoter region, where the specificity of activity is also at least similar to the specificity of activity of the reference promoter region. It should be noted that the term "equivalent" is not intended to exclude the case where the level and specificity of activity are significantly higher than those of the reference promoter region. For example, "having a promoter activity equivalent to that of the sequence shown as SEQ ID NO: 1" means that, when the GUS gene is expressed in protoplasts under conditions similar to those described in the following example of the present specification, the GUS activity is about 50% or more, preferably about 70% or more, and more preferably about 90% or more, of the GUS activity for the sequence shown as SEQ ID NO: 1, and that the activity is specifically expressed in anthers and/or pollen.

In the present specification, being "specifically" expressed in anthers and/or pollen means that a genetic product of interest is expressed, in at least either anthers or pollen, in an amount greater than in at least one kind of other tissue or organ of the same plant body. This means, for example, a genetic product being expressed in anthers and pollen in a greater amount than in a leaf blade in any portion of the same plant body. The specificity of expression as described can be evaluated by producing a transformed plant under conditions similar to those described in the following example of the present specification.

(Construction of an Expression Cassette and a Recombinant Plasmid as Well as Utilization of the Same)

A sequence including the CatA gene promoter region or active portions thereof that has been confirmed to be active may be incorporated into an appropriate expression vector for expression in plants. At the 3' terminus side of this sequence having been incorporated into an expression vector for expression in plants, an appropriate linker sequence (e.g., a linker having multiple cloning sites) is introduced, whereby an expression cassette which is suitable for a plant host can be produced. Accordingly, in the present specification, a "site for inserting a heterologous gene" means a site which is included within a linker or a sequence which functions similarly to a linker. The expression cassette may include other regulatory elements as desired. For example, a terminator sequence may be included in order to improve the expression efficiency or the like. The terminator sequence may be bond to the promoter sequence via the aforementioned linker sequence having multiple cloning sites.

A heterogenous gene which is intended to be expressed is expressibly linked 3' downstream of the promoter (e.g., at the multiple cloning sites) within the aforementioned expression cassette for expression in plants, whereby a recombinant plasmid is created. In the present specification, a "heterogenous gene" means any gene other than the CatA gene which is endogenous to rice or other plants, or any gene which is foreign to the plant, such that the expression of its genetic product is desired in anthers and/or pollen.

By employing a thus-created recombinant plasmid, a plant cell may be transformed. The transformation of the plant cell may be carried out by any methods known to those skilled in the art, e.g., a method using Agrobacteria, or an electroporation method to protoplasts. For example, the preparation of protoplasts of a plant cell may be carried out by following the method described in Kyozuka et al., Mol. Gen. Genet. 206:408–413(1987).

The transformed plant cell may be allowed to redifferentiate by usual methods, so as to give transformed plant tissue and eventually a plant body. In the preparation of a recombinant plasmid to be used for the transformation, the CatA gene promoter can be incorporated into a binary vector which is capable of being expressed in both a bacterial host and a plant host, for example. Such binary vectors are well-known to those skilled in the art. For example, by using a vector of a pBI system, including Agrobacterium expression systems, it is possible to utilize the infection system of microorganisms with respect to plants. By employing an appropriate recombinant plasmid, the heterogenous gene of interest can be introduced into any transformable plant, including monocotyledons, e.g., rice, and dicotyledons, e.g., tobacco.

As described above, the CatA gene promoter can induce specific expression in anthers and/or pollen. Accordingly, by employing as the heterologous gene that has a function of inhibiting the formation of anthers and/or pollen, it is possible to produce a male sterile plant. In the present specification, "a gene which has a function of inhibiting the formation of anthers and/or pollen" includes a gene whose genetic product is capable of inhibiting the formation of fertile pollen (e.g., genes coding for nuclease, protease, glucanase, etc.) and a gene which by itself exhibits a function of inhibiting the formation of anthers and/or pollen (e.g., antisense RNA of an endogenous gene which is expressed at the time of the formation of anthers and/or pollen, and ribozymes which can decompose such endogenous genes). Techniques for selecting male sterile plants and breeding of plants using such selection are well-known to those skilled in the art.

The aforementioned preparation of transformed plants may also be utilized for imparting plants with traits other than male sterility. For example, by employing a heterologous gene coding for a toxic protein, it is possible to control insect pests or the like which feed on pollen. Alternatively, by employing a heterologous gene coding for a protein which may become a nutrient, it is possible to enhance the nutritive value of a crop. The preparation of any useful plants which utilizes specific genetic expression in anthers and/or pollen falls within the present invention.

The present invention provides the use of a practical promoter which is highly active in anthers and/or pollen, from a rice gene. Accordingly, the present invention may be utilized not only for the breeding of rice but also the breeding of various other plants.

EXAMPLE

Hereinafter, the present invention will be described with respect to an example. However, the scope of the invention is not limited only to the example.

1. Isolation of Rice CatA Genomic Gene: Screening from a Genomic Library

A portion of CatA cDNA (Mori et al. (1992; supra)) was used for cloning the CatA genomic gene. An insert portion of a λ phage (clone No. 51), containing a non-full length cDNA (1.35 Kbp at the 3' side, lacking a total of about 0.45 Kbp including the 5' untranslated region and some of the coding region, out of the full 1.8 kbp) which was obtained during the cloning process of CatA cDNA, was amplified by PCR. From this phage, DNA was prepared and used as a template. As primers, λgt11-Forward Primer and λgt11-Reverse Primer (Toyobo) primers were used. The product was purified with Centricon-100 (Amicon), and adjusted to a concentration of 25 ng/10 μl, so as to be used as a probe for a Multiprime labeling method (Amersham).

A genomic DNA library of rice (Rice Genomic Library) which was commercially obtained from CLONTECH Laboratories Inc., Palo Alto, Calif. in the US was screened for the CatA gene. Following usual methods, phage λEMBL-3 comprising this genomic library was transfected into E.coli NM538 strain, and phage plaques were allowed to form. The phage plaques were transferred onto a nylon membrane, and were allowed to hybridize with the aforementioned probe under the standard conditions as follows. The probe was labeled with $^{32}P$.

Hybridization solution: 6×SSC-0.1% SDS, 5×Denhardt's, 100 microgram/ml salmon sperm DNA; hybridization temperature: 65° C.; hybridization time: overnight.

Next, the membrane was washed under the following conditions. Washing conditions: 2×SSC-0.1% SDS room temperature, 5 minutes plus 30 minutes; 1×SSC-0.1% SDS: 68° C., 1 hour.

After the washing, the nylon membrane was subjected to an autoradiography following usual methods, whereby the clones which had hybridized with the probe were detected. From the phages which were confirmed to have hybridized, DNAs were respectively prepared.

The DNAs of the aforementioned phages were digested with a combination of two or three kinds of restriction enzymes such as SalI and ScaI, and the digests were separated by agarose gel electrophoresis. The separated DNA fragments were transferred onto a nylon membrane, and allowed to hybridize with the aforementioned CatA cDNA fragment used as a probe. The hybridization conditions were the same as above, and the membrane was washed under the following conditions. Washing conditions: 2×SSC room temperature, 5 to 10 minutes, twice, 2×SSC-0.1% SDS, 65° C., 30 minutes.

After the washing, the nylon membrane was subjected to an autoradiography following usual methods, whereby the DNA fragments which had hybridized with the probe were detected.

There was a group of clones which had substantially the same signal intensity and band pattern, and therefore were presumed to have the same structure, as well as clones whose band patterns were only partially identical.

The clones which had substantially identical signal intensities and band patterns are considered to correspond to the CatA gene. The clones which lacked portions of the band patterns are considered to be clones whose CatA gene is partially deleted. The clones which had weak signals are considered to be genes for other catalases (isozymes) which have similar structures to that of CatA.

Through a detailed Southern analysis, an analysis of partial base sequences, a PCR analysis based on the CatA cDNA base sequence, etc., a clone λEM74/81 was obtained, in which the gene corresponding to CatA cDNA as well as an about 1.5 Kbp sequence 5' upstream thereto (which was presumably the promoter region) were contained.

The insert portion of clone λEM74/81 was cut out through HindIII and EcoRI digestion, and inserted into a sequencing vector designated pBluescript II KS+ or SK+ (Stratagene, CA). A number of plasmids including gradual deletions from the 5' side or the 3' side were prepared and their base sequences were determined. A 4,670 bp sequence was determined, its full sequence being shown as SEQ ID NO: 2.

Figure 1:
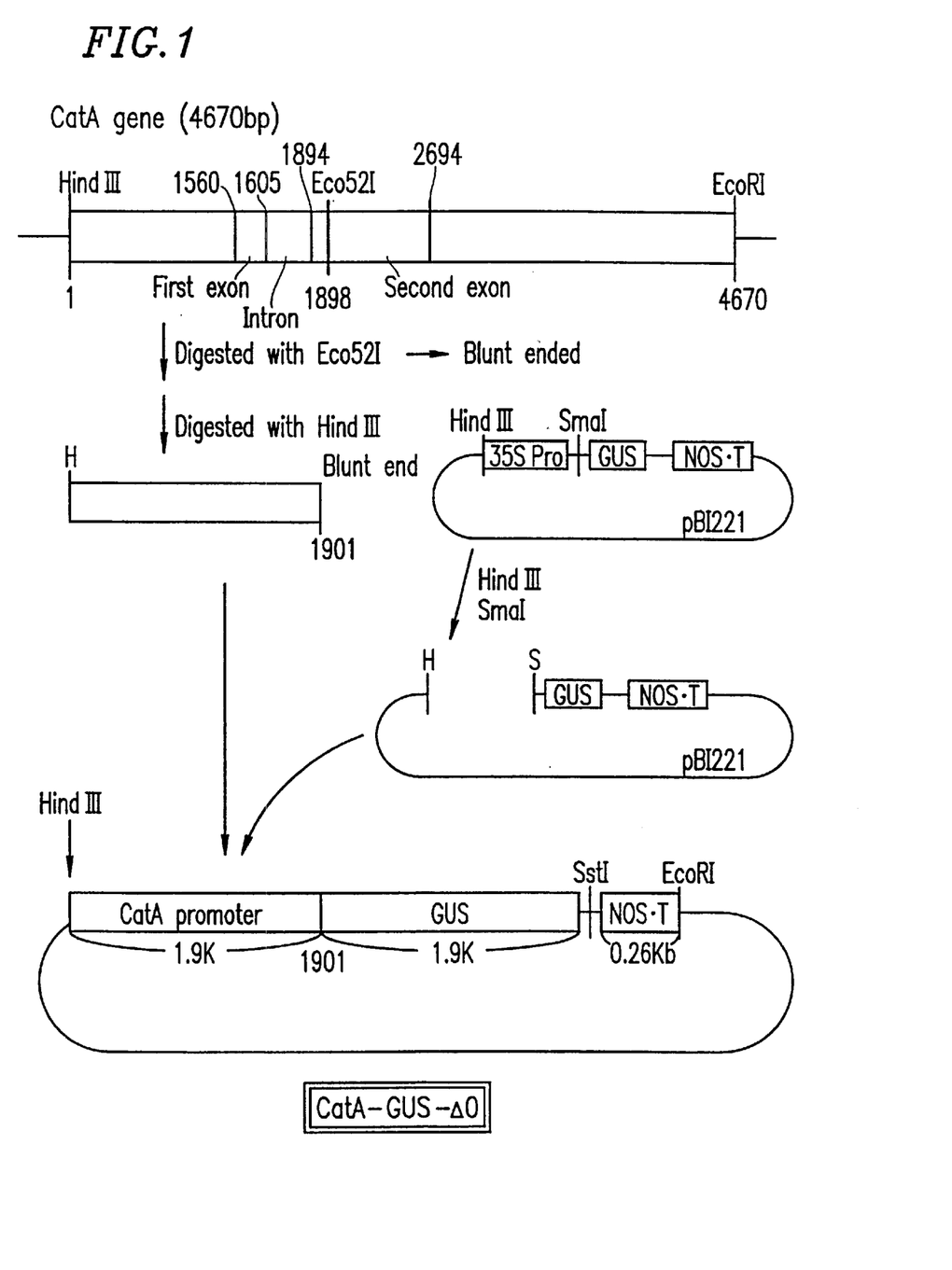
FIG. 1 is a schematic diagram illustrating the preparation of plasmid CatA-GUS-Δ0.

The base sequence of the genomic CatA gene has been published by the inventors (Journal of JAPAN SOCIETY FOR BIOSCIENCE, BIOTECHNOLOGY, AND AGRO-CHEMISTRY (1992; supra); and Higo et al. (1996; supra). A sequence of 4,670 bases from the HindIII restriction site to the EcoRI restriction site as shown in FIG. 1 has been registered in DDBJ, an international DNA base sequence data base (Accession No. D29966). A sequence of 4,676 bases, which additionally includes a preceding HindIII recognizing sequence and a succeeding EcoRI recognizing sequence, has been published in Higo et al. (1996; supra).

2. Preparation of a Recombinant Plasmid Having the CatA Gene Promoter

The CatA gene obtained in 1. above was 4,670 bp long. It was found that the first exon exists at positions 1,560 to 1,605 of SEQ ID NO: 2; the second exon exists at positions 1,894 to 2,694 of SEQ ID NO: 2; the third exon exists at positions 2,781 to 3,380 of SEQ ID NO: 2; the fourth exon exists at positions 3,730 to 4,117 of SEQ ID NO: 2; and that the first to third introns exist between these exons.

Based on this sequence information, a region which is presumed to be the promoter can be cut out.

FIG. 1 shows the preparation of a plasmid CatA-GUS-Δ0, which contains the rice CatA gene promoter.

Clone λEM74/81 was digested with Eco52I and blunt-ended, and then digested with HindIII, and subjected to agarose electrophoresis to recover an about 1.9 Kbp fragment. A fragment having a sequence from position 1 to position 1901 of the insertion sequence within clone λEM74/81 was obtained. This fragment contained a sequence upstream of the first exon, the first intron, and a portion of the second exon. The 5' end of the fragment was the HindIII site, and the 3' end was a blunt end.

pBI221, an expression vector for expression in plant cells (CLONTECH Laboratories Inc., Palo Alto, Calif.) includes the cauliflower mosaic virus (CaMV)35S promoter, the β-glucuronidase (GUS) coding region, and the nopaline synthase terminator (NOS-T). This pBI221 was digested with HindIII and SmaI, and the larger fragment was recovered. This larger fragment was a fragment of pBI221 in which the 35S promoter region of CaMV had been deleted. This fragment was linked to a fragment having the sequence from position 1 to position 1901 of the aforementioned insertion sequence within clone λEM74/81, whereby CatA-GUS-Δ0 was produced. This method has already been published by the inventors together with the base sequence of the CatA gene (Higo et al. (1996: supra)).

3. Transformation of Rice Cultured Cell Protoplasts and Expression of the GUS Gene The plasmid obtained in 2. above was introduced into the protoplasts of rice cultured cells (Oc cells), in the manner described in Higo et al. (1996; supra). As a control, pBI221 was used.

The method for preparing protoplasts from rice cultured cells (Oc cells), transformation of protoplasts by electroporation, and measurement of GUS gene expression using a protoplast extract were carried out following the manner described in Higo et al. (1996; supra).

Figure 2:
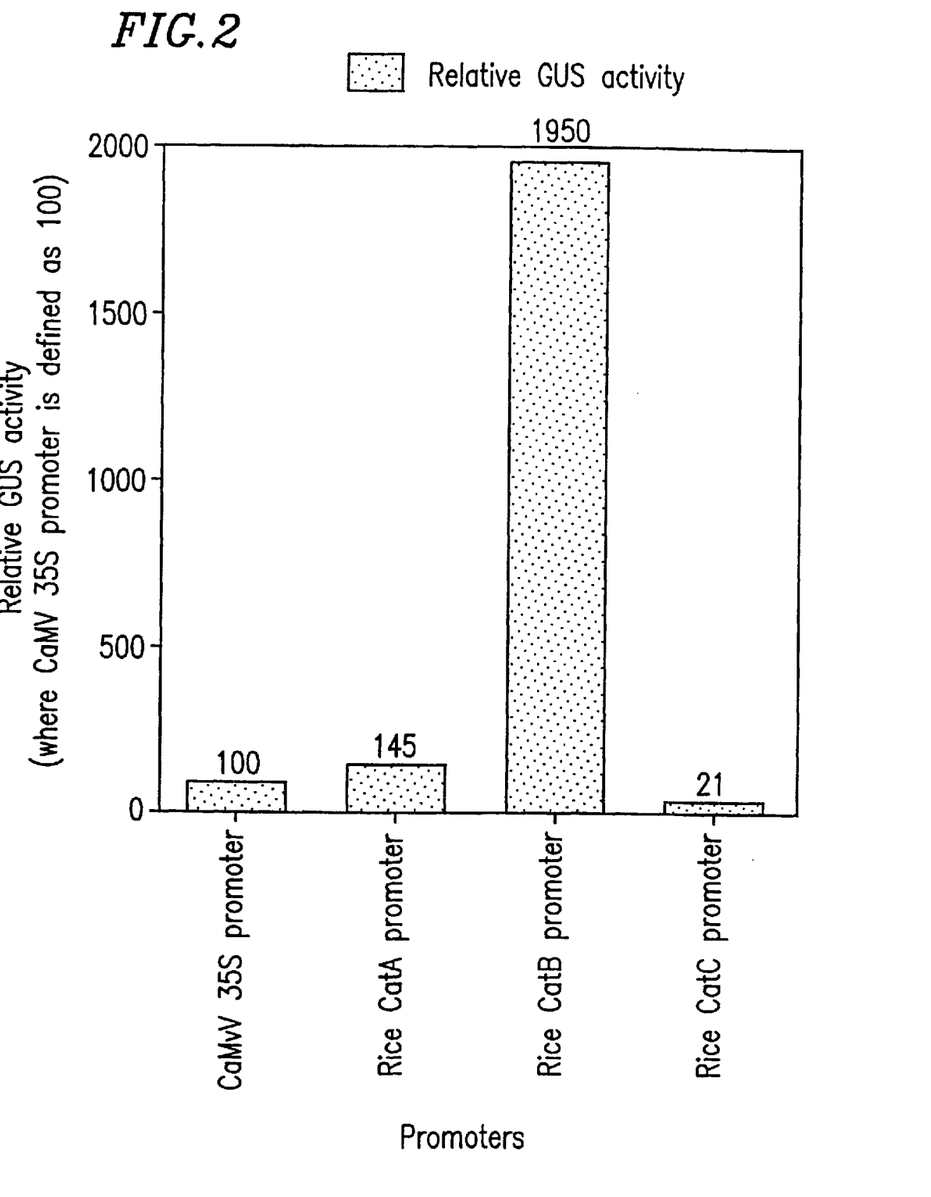
FIG. 2 is a diagram in which the activities of various promoters are compared.

The results are shown in FIG. 2. According to these results, the CatA gene promoter exhibited an activity which is about 1.5 times higher than that of the control, i.e., CaMV 35S promoter.

4. Preparation of Transformed Rice (To Generation)

By using CatA-GUS-Δ0 plasmid, which was confirmed to have a high activity in the protoplasts of rice cultured cells (Oc cells) in 3. above, rice was transformed in the following manner.

Basically following the method of Akagi et al. (Mol. Gen. Genet. 215:501–506(1989)), suspension cells were established from a rice plant (cultivar: Kinuhikari) Then, protoplasts were prepared from theses suspension cells. The plasmid was introduced by an electroporation technique (basically according to Tada et al., Theor. Appl. Genet. 80:475–480(1990)) into the protoplasts. The protoplasts were redifferentiated (basically according to Fujimura et al., Plant Tissue Culture Lett. 2:74–75(1985)). After selection based on GUS staining, transformed rice plants were obtained. The details are described below.

1) Callus Induction from Rice Scutella 1.1) A medium was prepared as follows:

① To an MS basic medium, 2 ppm 2,4-D, 0.1% casein hydrolysate, and 3% sucrose were added, and the medium was adjusted to pH5.5. ② 1% agar was added to the medium and the medium was autoclaved. ③ The medium was dispensed into deep φ9 cm petri dishes (about 40 ml/dish) within a clean bench.

1.2) Seeds were sterilized as follows:

① Kinuhikari seeds were husked, and the brown rice grains were taken out. ② The brown rice grains were placed in a 50 ml beaker, and immersed in 70% ethanol for 30 seconds. ③ The brown rice grains were rinsed three times in tap water. ④ The brown rice grains were sterilized in 5% sodium hypochlorite (with a few drops of Tween 20 added) for 20 minutes. ⑤ The brown rice grains were rinsed three times in sterilized water. ⑥ The brown rice grains were placed on an agar medium by using tweezers (9 grains/φ9 cm petri dish). ⑦ The brown rice grains were cultured at about 300 lux, 26° C. for about 1 month.

2) Establishment of Suspension 2.1) A medium was prepared as follows:

① To a basic medium including R2 inorganic salts and B5 vitamins, 1 ppm 2,4-D, 3% sucrose, and 0.3% casein hydrolysate were added, and the medium was adjusted to pH5.5. ② 20 ml of the medium was dispensed into 100 ml culture flasks, and sterilized in an autoclave.

2.2) A suspension was established as follows:

① Friable calli derived from the scutellum of a mature seed were transferred into a liquid medium. ② The flask containing the calli was rotated at 80 rpm at 26° C. under weak light. ③ On the third day following transfer, the medium was exchanged with a fresh one. ④ The culture was continued for 4 more days. ⑤ Using a callus culture pipet, the calli were dispersed, and only the actual callus portions were transferred. ⑥ The calli were transferred on a fresh medium every week.

3) Introduction of the Gene into Protoplasts
3.1) An enzyme solution was prepared as follows:
① 4 g of Cellulase onozuka RS, 1 g of Macerozyme R-10, 0.5 g of CaCl$_2$.2H$_2$O, and 7.28 g of Mannitol were placed in a 100 mL beaker and mixed. Water was added to the mixture, and the mixture was stirred with a stirrer to effect dissolution. ② The mixture was adjusted to pH5.5, and filled up to 100 mL. ③ After leaving the mixture at 37° C. for 20 minutes, the mixture was centrifuged at 12000 rpm for 15 minutes. ④ 10 mL of supernatant was dispensed into each centrifuge tube, which was sealed with a Parafilm, and frozen and preserved. ⑤ The supernatant was dissolved in a hot water bath, and subjected to filtration sterilization.
3.2) Protoplast was isolated as follows:
① Suspension cells available on the fourth day of culture were used. ② Using a callus culture pipet, only the suspension cells (about 10 g) were transferred to a 100 mL flask with 10 mL of the enzyme solution. ③ The flask was left for 5 hours in an incubator at 27° C.
3.3) The protoplasts were purified as follows:
① The flask was lightly rotated so as to allow the cells at the bottom to float. ② The floating cells were quickly decanted onto a 155 μm mesh. ③ The mesh was slightly shaken up and down to wait for the enzyme solution to completely pass through. ④ The filtrated enzyme solution was directly decanted out of the beaker onto a 77 μm mesh. ⑤ The mesh was slightly pulled up, so as to allow the enzyme solution to pass through. ⑥ The filtrated enzyme solution was again decanted onto a 31 μm mesh. ⑦ The mesh was slightly pulled up, so as to allow the enzyme solution to pass through. ⑧ The enzyme solution was transferred from the beaker into a centrifuge tube by decanting. ⑨ A centrifugation was performed at 600 rpm for 1 minute. ⑩ The supernatant was transferred into a new centrifuge tube with a disposable pipet. ⑪ A centrifugation was performed at 900 rpm for 3 minutes. The supernatant was discarded. ⑫ 0.4 M glucose was poured into the centrifuge tube along its wall, and the protoplasts were suspended. ⑬ A centrifugation was performed at 900 rpm for 3 minutes. The supernatant was discarded. ⑭ AA buffer was poured into the centrifuge tube along its wall, and the protoplasts were suspended. ⑮ A centrifugation was performed at 900 rpm for 3 minutes. The supernatant was discarded. ⑯ A small amount of AA buffer was poured into the centrifuge tube along its wall. ⑰ The protoplasts were counted by using a hemocytometer. ⑱ The fluid amount of the protoplast suspension was measured. ⑲ The protoplast density was adjusted to 1×10$^7$ cells/mL by using AA buffer, wherein the AA buffer was as follows: 35 mM K-Aspartic acid, 5 mM Ca-Gluconate, 5 mM Mg-Asparatic acid, 5 mM MES, 0.4 M mannitol, pH5.8 (adjustment is unnecessary).
3.4) The gene was introduced as follows:
① An electroporation chamber was sterilized with 70% ethanol. ② The plasmid (1 μg/μL) which had been dissolved in TE was added to the protoplast suspension. The final concentration of the added plasmid was as follows: 50 μg/mL of HPT2 (hygro); and 100 μg/mL of CatA-GUS-Δ0. The structure of the plasmid HPT for hygromycin selection has been reported (Tada et al., Theor. Appl. Genet. 80:475–480(1990)). ③ The test tube was placed upright on ice, and left for 20 minutes. ④ The protoplasts were transferred into the chamber. ⑤ Electricity which had been charged in a capacitor was discharged. The discharge conditions were: 880 μF, 475 V/cm; and the time constant was about 30 msec. ⑥ After the protoplasts were left for 10 seconds or more, they were recovered into a centrifuge tube. ⑦ The protoplasts were left at room temperature for 20 minutes.

3.5) Protoplasts were cultured as follows:
① The protoplasts were centrifuged at 900 rpm for 3 minutes. The supernatant was discarded. ② c-med was poured into the centrifuge tube along its wall, and the protoplasts were suspended. The protoplasts were adjusted to 1×10$^6$ cells/mL with c-med. Only the medium was recovered from the suspension on the third day c-med culture, and the floating matter was removed at 12000 rpm. To 40 mL of the medium, 200 μL of 2,4-D (100 ppm), 400 μL of B5 vitamins, and 5.46 g of sucrose were added, and adjusted to pH4.3. The medium was frozen and preserved. The medium was thawed immediately before use, and subjected to filtration sterilization. ③ 750 μL of the culture was dispensed in each coating dish (Falcon #3002). ④ The culture was spread over the entire dish by using a Conradi stick. ⑤ The dish was sealed with a Parafilm. ⑥ The dishes were placed in a Tupperware. In order to prevent the culture from drying, a beaker or the like containing water was also included in the Tupperware. ⑦ The culture was incubated in a dark place at 27° C.
4) Regeneration of Transformed Plants
4.1) The transformed cells were selected and grown as follows:
① On the 14th day of culture, 600 μL of a GI medium was added. The GI medium was obtained by adding 2 ppm 2,4-D 0.4 M glucose to an R2 medium and adjusting it to pH4.9. ② In order to select hygromycin-resistant calli, 50 μg/mL of hygromycin was added to the GI medium. ③ Two weeks after the addition of the GI medium, the calli that had grown were transferred onto a GII agar medium. The GII agar medium was obtained by adding 2 ppm 2,4-D, 3% sucrose to an R2 medium, adjusting it to pH4.9, and thereafter adding 1% agar to the medium and autoclaving it, 10 mL of the medium being dispensed into each φ9 cm×10 mm petri dish.
4.2) The transformed plant was regenerated as follows:
① A medium containing N6 inorganic salts, B5 vitamins, 3% sucrose, NAA 1 ppm, kinetin 4 ppm, 3% sorbitol, and 0.03% casein hydrolysate was adjusted to pH5.8. 1.5% agar was added and the medium was autoclaved. ② The medium was dispensed into deep φ90 mm×20 mm plastic petri dishes (40 mL–50 mL/dish) within a clean bench. ③ The calli which had grown to a diameter of about 3 mm were transferred onto the agar medium. ④ About 20 calli were placed on each dish. ⑤ The calli were cultured at 27° C. under continuous light of 3000 lux. Plants were regenerated in about 4 weeks. ⑥ Among the plants which had differentiated on the differentiation medium, those which had shoots grown to about 3 cm long were transferred into Magenta-type vessels with its roots. Nine shoots were transferred into each box. The medium was obtained by adding 1% sucrose to a 1/2 MS medium and adjusting it to pH5.8. After adding 0.15% Gelrite and thermally melting the medium, 50 mL of the Gelrite was dispensed into each Magenta-type vessel and autoclaved. ⑦ The shoots with roots were cultured at 27° C. under continuous light of 10000 lux. ⑧ In about a week, shoot tip ends entirely reached the lid. In some cases, divalent cations in the medium may be lost so that the medium may become liquidized.

The redifferentiated individuals (T0 generation rice) obtained in the aforementioned manner were transferred into a pot. Among the grown-up individuals, those in which GUS had been expressed were selected, as determined by GUS tissue staining of their leaves.

The GUS staining for selecting the transformed plants was performed in the following procedure: ① staining solution containing 1 mM X-Gluc, 50 mM sodium phosphate buffer (pH7.0), and 10% Me-OH was prepared. ② 500 µL of the staining solution obtained from ① was dispensed in each of 2 mL microtubes. ③ slices of leaves of the regenerated plants were placed in the microtubes. ④ The microtubes were incubated at 37° C. for 24 hours. ⑤ Chlorophyll was removed with 70% Et-OH. ⑥ The rice plants which had been GUS-stained were selected.

Thus, 15 individuals of T0 generation rice plants in which GUS was expressed in their leaves were selected, and their seeds collected (T1 generation seeds).

5. PCR Selection of T1 generation rice plants Among the 15 lines obtained in 4. above, the unhulled T1 seeds of 10 lines were treated with 1% antiformin for 1 hour, and thereafter immersed in tap water for 2 days, and sown on granular soil (BONSORU No. 1, Sumitomo Chemical). From the leaf blades of the seedlings, DNA was extracted by using ISOPLANT (Nippon Gene). Using the extracted DNA as a template, a PCR was carried out, with a primer F1813 (5'-CATGGCTGGTTGATTCAGC-3': a sequence within the CatA first intron) and a primer R2368 (5'-CGTCGGTAATCACCATTCC-3': a sequence within the GUS gene coding region), to examine whether or not the introduced DNA sequence was present. PCR's were carried out by using AmpliTaq Gold (Perkin Elmer), a DNA polymerase. The reaction conditions were as follows: after performing a treatment at 94° C. for 12 minutes, 35 cycles were performed, each cycle consisting of a treatment at 94° C. for 1 minute, a treatment at 55° C., for 2 minutes, and a treatment at 72° C. for 3 minutes.

The reaction solution was subjected to electrophoresis in 1% agarose, stained with ethidium bromide, and irradiated with ultraviolet light, whereby the presence/absence and size of any PCR products were determined. Thus, the T1 generation plants in which the gene had successfully been introduced were selected.

In order to confirm whether or not the introduced GUS gene was being expressed, the GUS activity of the leaf blades of the T1 plants was examined by the following GUS tissue staining method.

As the method of GUS tissue staining for rice leaf blades for observing GUS activity, a method was carried out which was partially modified from a method described in "EXPERIMENTAL PROTOCOLS FOR OBSERVING PLANT CELLS: FROM GENE EXPRESSION TO INTRACELLULAR STRUCTURE AND FUNCTION"; Cell Technology special edition, Plant Cell Technology series 62-3; METHOD FOR DETECTING GUS ACTIVITY AT THE CELLULAR LEVEL (Misa TAKAHASHI, Hiromichi MORIKAWA) pp.71–79 (supervised by Hiroo FUKUDA, Mikio NISHIMURA, Kenzo NAKAMURA).

The procedure was as follows: ① X-Gluc solution [100 mM phosphate buffer (pH 7.0), 1 mM X-Gluc, 0.3 mM potassium ferricyanide, 0.3 mM potassium ferrocyanide, 0.2% Triton-X100] was prepared. ② 500 µL of the X-Gluc solution was dispensed in each well of a 24-well titer plate. ③ Each tissue sample or slice of the rice plants was placed in a well, and treated at 28° C. for 16 hours. ③ The X-Gluc solution was removed, and a decolorization was performed with 70% ethanol. ④ The 70% ethanol was removed, and the tissue sample or slice was immersed in a 50% glycerol solution. ⑤ A microscope or a stereoscopic microscope was used for observation.

The T1 generation plants were divided into groups according to the expression level of the GUS gene in their leaves. The seeds of the plants which showed a high expression level in their leaves were collected (T2 generation seeds).

6. Sowing of T2 Seeds, PCR Selection of Transformants, and GUS Tissue Staining

The unhulled seeds of the T2 transformants were treated as mentioned above and sown. DNA was extracted from the leaf blades of their seedlings in the aforementioned manner, and a PCR was carried out to determine whether or not the introduced DNA sequence was present. It was confirmed that about half of the T2 plants examined were transformants having the introduced GUS gene.

In order to confirm whether or not the introduced GUS gene was being expressed, the GUS activity of the leaf blades of the seedlings of the T2 plants was examined in the aforementioned manner. For all of the T2 transformants in which the presence of the GUS gene had been confirmed by PCR, GUS activity was observed in their leaf blades. The plants in which the GUS gene expression was confirmed in their leaf blades were allowed to continue growing, and their anthers were collected during a flowering stage to examine the GUS activity in the anthers and pollen.

Figure 3:
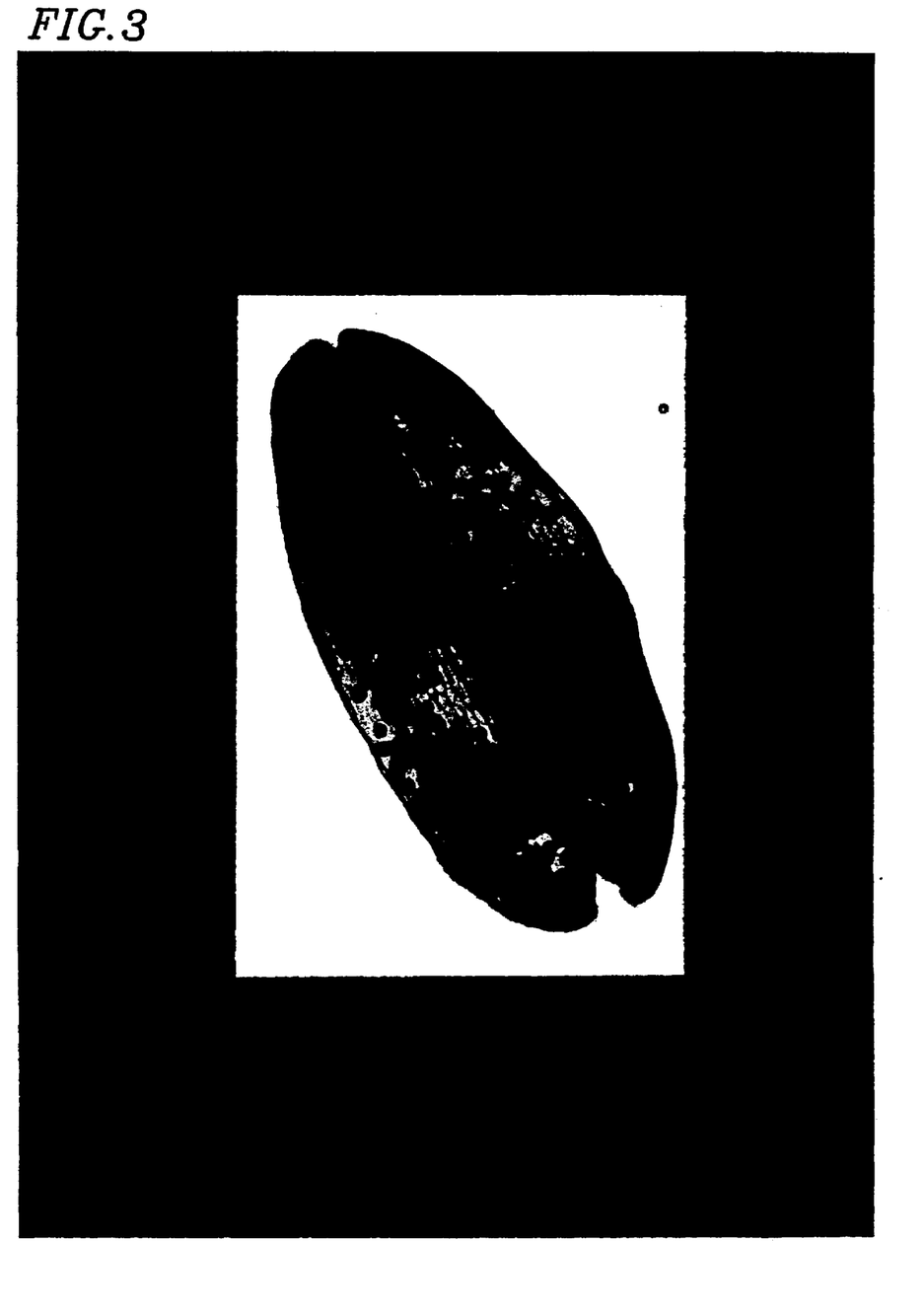
FIG. 3 is a photograph showing a GUS tissue staining result for an anther.
Figure 4:
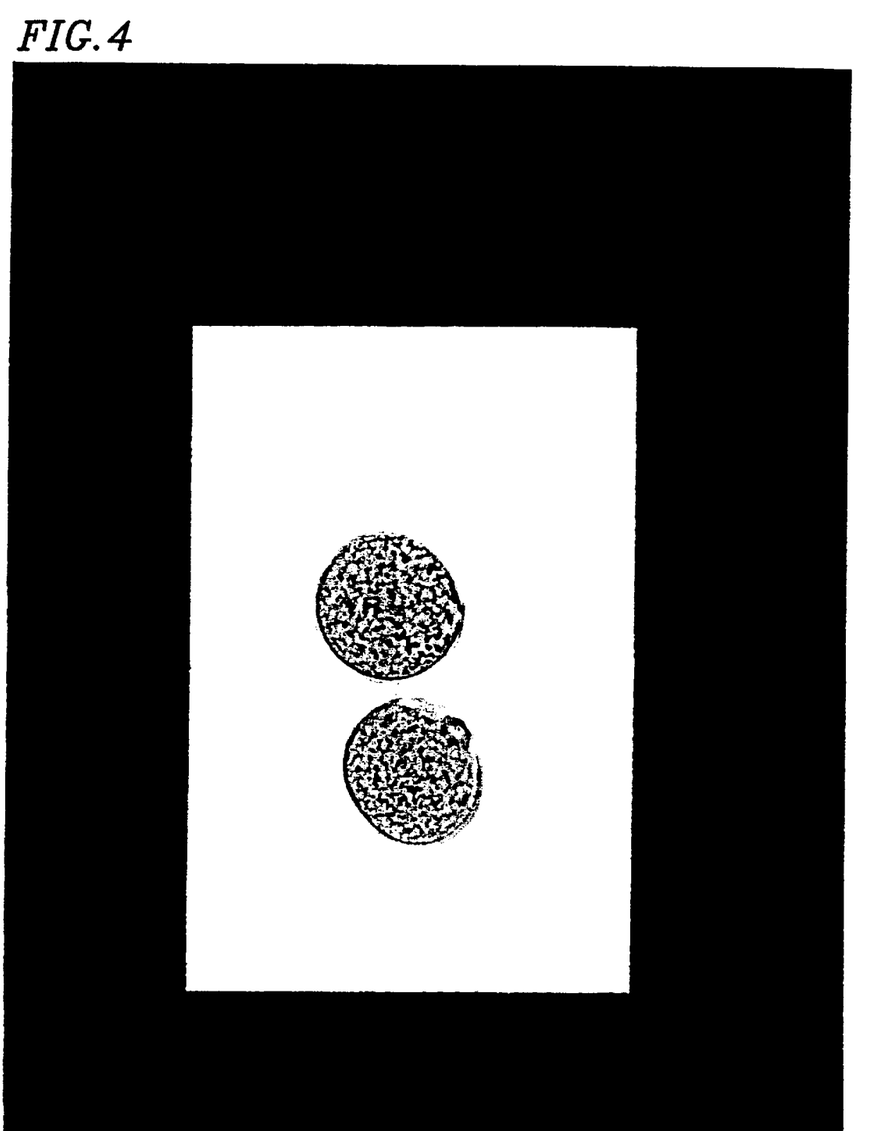
FIG. 4 is a photograph showing a GUS tissue staining result for pollen.

The results are shown in FIGS. 3 and 4. The GUS activity as examined by collecting anthers during a flowering stage indicated a higher GUS activity than in the leaf blades. As a result of the observation of anthers and pollen by microscope, it was found that the anther walls (FIG. 3) and the interior of the outer coat of pollen (FIG. 4) had be been stained blue due to GUS activity.

INDUSTRIAL APPLICABILITY

The CatA gene promoter according to the present invention has a very high activity in anthers and pollen. Accordingly, the present invention is useful for the breeding of plants, e.g., rice, through genetic engineering of anthers and/or pollen.

What is claimed is:

1. A method for specifically expressing a heterologous gene in the anthers of a plant, comprising the steps of:
   providing an expression vector comprising:
   a rice CatA gene promoter region having a sequence shown as SEQ ID NO: 1, or a portion thereof which has promoter activity equivalent to that of the sequence shown as SEQ ID NO: 1, and
   an insertion site for inserting a gene such that the gene is operably linked to the promoter region;
   inserting the heterologous gene into the insertion site to form a recombinant expression vector;

transforming a plant cell with the recombinant expression vector; and redifferentiating the transformed plant cell to obtain a plant body.

2. A method for specifically expressing a heterologous gene in the pollen of a plant, comprising the steps of:

providing an expression vector comprising:

a rice CatA gene promoter region having a sequence shown as SEQ ID NO: 1, or a portion thereof which has a promoter activity equivalent to that of the sequence shown as SEQ ID NO: 1, and an insertion site for inserting a gene such that the gene is operably linked to the promoter region;

inserting the heterologous gene into the insertion site to form a recombinant expression vector;

transforming a plant cell with the recombinant expression vector; and redifferentiating the transformed plant cell to obtain a plant body.

* * * * *